(12) United States Patent
Brophy et al.

(10) Patent No.: US 8,338,325 B2
(45) Date of Patent: Dec. 25, 2012

(54) TETHERED CATALYST PROCESSES IN MICROCHANNEL REACTORS AND SYSTEMS CONTAINING A TETHERED CATALYST OR TETHERED CHIRAL AUXILIARY

(75) Inventors: John H. Brophy, Bristol (GB); Kai Jarosch, Bexley, OH (US)

(73) Assignee: Velocys, Inc., Plain City, OH (US)

( * ) Notice: Subject to any disclaimer, the term of this patent is extended or adjusted under 35 U.S.C. 154(b) by 1050 days.

(21) Appl. No.: 10/642,439

(22) Filed: Aug. 14, 2003

(65) Prior Publication Data

US 2004/0132613 A1 Jul. 8, 2004

Related U.S. Application Data

(60) Provisional application No. 60/403,952, filed on Aug. 15, 2002.

(51) Int. Cl.
*B01J 21/00* (2006.01)
*B01J 23/00* (2006.01)
*B01J 25/00* (2006.01)
*B01J 29/00* (2006.01)
*B01J 31/00* (2006.01)
*B01J 21/04* (2006.01)
*B01J 23/02* (2006.01)

(52) U.S. Cl. ............... 502/150; 502/100; 502/439

(58) Field of Classification Search ............... 502/158, 502/159, 166–168, 150, 170, 439, 523, 527.11, 502/527.16–527.19, 527.23, 527.24, 100
See application file for complete search history.

(56) References Cited

U.S. PATENT DOCUMENTS

| | | | |
|---|---|---|---|
| 3,933,438 A | 1/1976 | Bowler et al. | |
| 3,993,855 A * | 11/1976 | Kang | 525/338 |
| 4,394,294 A * | 7/1983 | Gryaznov et al. | 502/158 |
| 4,960,745 A * | 10/1990 | Johnson | 502/150 |
| 5,080,771 A | 1/1992 | Novotny et al. | |
| 5,171,898 A | 12/1992 | Arntz | |
| 5,314,827 A | 5/1994 | Schmidt et al. | |
| 5,373,725 A | 12/1994 | Sironi et al. | |
| 5,451,704 A | 9/1995 | Ho et al. | |
| 5,753,143 A | 5/1998 | Bhat et al. | |
| 5,766,954 A | 6/1998 | Freedman et al. | |
| 5,778,664 A | 7/1998 | Janata et al. | |
| 5,783,741 A | 7/1998 | Ellis et al. | |
| 5,789,333 A | 8/1998 | Angelici et al. | |
| 5,811,515 A | 9/1998 | Grubbs et al. | |
| 5,932,791 A | 8/1999 | Hambitzer et al. | |

(Continued)

FOREIGN PATENT DOCUMENTS

DE 19950952 A1 4/2001

(Continued)

OTHER PUBLICATIONS

"Enzymatic Microreactors," Ackerman et al., http://pnl.gov/microcats/aboutus/research/enzymatier.html, Mar. 2001.

(Continued)

*Primary Examiner* — James McDonough
(74) *Attorney, Agent, or Firm* — Frank Rosenberg

(57) ABSTRACT

The invention provides systems and methods for conducting reactions in which a reactant contacts a tethered catalyst and/or tethered chiral auxiliary in a microchannel and is converted to product.

29 Claims, 5 Drawing Sheets

U.S. PATENT DOCUMENTS

| | | | |
|---|---|---|---|
| 6,028,025 A | 2/2000 | Ying et al. | |
| 6,040,261 A | 3/2000 | Hlatky | |
| 6,087,293 A | 7/2000 | Carnahan et al. | 502/158 |
| 6,197,714 B1 | 3/2001 | Bansleben et al. | |
| 6,251,280 B1* | 6/2001 | Dai et al. | 210/656 |
| 6,316,616 B1 | 11/2001 | Jacobsen et al. | |
| 6,414,836 B1 | 7/2002 | Tennet et al. | |
| 6,455,458 B1 | 9/2002 | Canich | 502/117 |
| 6,488,838 B1* | 12/2002 | Tonkovich et al. | 208/108 |
| 6,660,890 B1 | 12/2003 | Studer | 568/599 |
| 6,830,736 B1* | 12/2004 | Lamla et al. | 422/211 |
| 7,005,405 B2* | 2/2006 | Suenaga et al. | 502/439 |
| 2001/0056190 A1 | 12/2001 | Goossen et al. | |
| 2002/0055655 A1* | 5/2002 | Leipprand et al. | 568/313 |
| 2002/0182603 A1* | 12/2002 | Chapman et al. | 435/6 |
| 2003/0036474 A1* | 2/2003 | Ostoja-Starzewski et al. | 502/152 |
| 2004/0019212 A1* | 1/2004 | Hoveyda et al. | 546/2 |
| 2004/0220434 A1* | 11/2004 | Brophy et al. | 568/959 |
| 2007/0141550 A1 | 6/2007 | Zare et al. | |
| 2007/0141616 A1 | 6/2007 | Sudo | |

FOREIGN PATENT DOCUMENTS

| | | |
|---|---|---|
| DE | 10031381 A1 | 1/2002 |
| WO | WO 02/068454 A2 | 9/2002 |
| WO | WO 2004/028685 A2 | 4/2004 |
| WO | WO 2004/067492 | 8/2004 |

OTHER PUBLICATIONS

"Base catalysts immobilised on silica coated reactor walls for use in continuous flow systems," Jackson, et al., Green Chem., 6, 193-195 (2004).

PCT International Search Report, PCT/US03/25442, mailed Nov. 20, 2003.

"The use of a novel microreactor for high throughput continuous flow organic synthesis," Greenway et al., Sensors and Actuators B, pp. 153-158 (2000).

"An investigation of Knoevenagel condensation reaction in microreactors using a new zeolite catalyst," Zhang et al., Applied Catalysis A: General 261, pp. 109-118 (2004).

"Knoevenagel condensation reaction in a membrane reactor," Lai et al., Chem. Commun. pp. 218-219 (2003).

"Technology and Applications of Microengineered Reactors," Gavriilidis et al., Trans. IchemE, vol. 80, Part A, pp. 3-30 (Jan. 2002).

Haswell et al., "Kumada-Corriu reactions in a pressure-driven microflow reactor," Lab on a Chip, 1, 164-166 (Aug. 2001).

Pennemann et al., "Benchmarking of Microreactor Applications," Organic Process Res. Dev., 8, 422-439 (2004).

Watts et al., "The application of micro reactors for organic synthesis," Chem. Soc. Rev., 34, 235-246 (Feb. 2004).

Wiles et al., "Acid-catalysed synthesis and deprotection of dimethyl acetals in a miniturised electroosmotic flow reactor," Tetrahedron, 61, 5209-5217 (Apr. 2005).

Wiles et al., "An investigation into the use of silica-supported bases within EOF-based flow reactors," Tetrahedron, 60, 8421-8427 (2004).

Claus et al., "Miniaturizatoin of screening devices for the combinatorial development of heterogensous catalysts," Catalysis Today, 67, pp. 319-339 (2001).

Jones et al., "Dehydrogenation of cyclohexane to benzene in microreactors," in Microfluidic Devices and Systems II, pp. 160-168 (1999).

Beretta et al., "Production of olefins via oxidative dehydrogenation of light paraffins at short contact times," Catalysis Today, 64, pp. 103-111 (2001).

Zhou et al., "Oxidative dehydrogenation of propane over mesoporous HMS silica supported vanadia," Catalyst Letters, 75 pp. 107-112 (2001).

Steinfeldt et al., "Comparative studies of the oxidative dehydrogenation of propane in micro-channels reactor module and fixed-bed reactor," Studies in Surface Science and Catalysis, pp. 185-190 (2001).

Cong et al., "Combinatorial discovery of oxidative dehydrogenation catalysts within the Mo-V-Nb-O system," Proc. Natl. Acad. Sci. USA, 96, pp. 11077-11080 (1999).

Liu et al., "Discovery from combinatorial heterogeneous catalysis A new class of catalyst for ethane oxidative dehydrogenation at low temperatures," Appl. Catal. A. 254, pp. 59-66 (2003).

Cui et al. "Fabrication of microreactors for hehydrogenation of cyclohexane to benzene," in Sensors and Actuators B—Chemical 71 pp. 228-231 (2000) abstract only.

Wolfrath et al., "Novel Membrane Reactor with Filamentous Catalytic Bed for Propane Dehydrogenation," 40, pp. 5234-5239 (2001).

Venkataraman et al., "Millisecond catalytic wall reactors: dehydrogention of ethane," Chem. Eng. Sci., 57 pp. 2335-2343 (2002).

Euzen et al., "Deactivation of palladium catalyst in catalytic combustion of methane," Catalysis Today, 47 pp. 19-27 (1999).

Kestenbaum et al., "Synthesis of ethylene oxide in a microreaction system," in IMRET 3 Proceedings of the Third international Conf. on Microreaction Technology 207-212 (1999).

Lai et al., "Knoevenagel condensation reaction in a membrane microreactor," Chem Comm. pp. 218-219 (published on web Dec. 2002).

* cited by examiner

US 8,338,325 B2

TETHERED CATALYST PROCESSES IN MICROCHANNEL REACTORS AND SYSTEMS CONTAINING A TETHERED CATALYST OR TETHERED CHIRAL AUXILIARY

RELATED APPLICATIONS

In accordance with 35 U.S.C. sect. 119(e), this application claims priority to U.S. Provisional Application No. 60/403,952, filed Aug. 15, 2002, which is incorporated herein as if reproduced in full below.

FIELD OF THE INVENTION

The present invention relates to chemical conversions catalyzed and/or mediated by tethered catalyst compositions and carried out in a microchannel reactor. The invention further relates to a catalyst systems comprising a microchannel reactor containing a tethered catalyst composition.

INTRODUCTION

Homogeneous catalysts are used widely in the synthesis of, inter alia, organic chemicals, fine chemicals and pharmaceutical intermediates. The structure of such catalysts can be varied by incorporation of different ligands or other functional groups, and activity can be tailored to suit the particular reaction and desired products. Homogeneous catalysts, by definition, are present in the same phase as at least one of the reactants undergoing catalytic conversion. Ordinarily, homogeneous catalysts dissolve in the reaction medium or solvent used to carry the reactants, thus allowing for good contact between the catalyst and reactants, high activity, and selectivity to the desired products. However, this very solubility is also a major drawback. Because of their relatively high cost, especially those homogeneous catalysts containing expensive metals and complex ligands, they must be recovered from the reaction products for re-use. In many cases the process of recovering the catalyst can lead to its decomposition. Catalyst recovery also introduces additional process steps and capital costs.

Conventional heterogeneous catalysts, by definition, do not dissolve in the reaction medium and, therefore, are easier to separate from the products with considerable savings in energy and capital costs. However, conventional heterogeneous catalysts are frequently not as active or selective as homogeneous catalysts.

Over the past twenty five years there have been many attempts to "heterogenize" homogeneous catalysts, that is, fix or otherwise immobilize an ordinarily homogenous catalyst into a solid phase. This is done with the aim of combining the activity and selectivity of the homogeneous catalyst with the ease of separation and recovery of the heterogeneous catalyst. However these catalysts are not widely used because of their low activity compared to their homogeneous equivalents.

One such approach of heterogenizing involves polymer based catalysts. Commercially available polymer supported tri-phenyl phosphine has been used for immobilizing cobalt-phosphine complexes and arene-ruthenium complexes. The polymer supported cobalt phosphine complex has been shown to be an effective catalyst for the oxidation of primary and secondary benzylic alcohols (to aldehydes and ketones) using t-butyl hydroperoxide as oxidant. Attachment of the metal complex had little effect on yields compared to the homogeneous reaction but does reduce the amount of acid formed in primary alcohol oxidation. A resin bound ruthenium complex of $RuCl_2(PPh_3)_3$ shows high activity in the oxidation of unsaturated hydrocarbons and the transfer hydrogenation of ketones. Again the attachment to a support had little effect on the yields of the reaction. Even when reused, yields for the supported catalyst remain around 85%. In this case a small proportion of the catalyst comes off during the reaction but returns to the support on cooling. Polymer supported reagents and catalysts have been used more recently to generate libraries of compounds for high throughput screening in pharmaceutical applications. One example is tetra-n-propylammonium perruthenate (TPAP) which has been attached onto an Amberlyst resin by ion exchange and demonstrated in the catalytic oxidation of alcohols to aldehydes, as reported in *Synthesis*, pp. 977-979 (1998). Problems with polymer decomposition limited the number of times the catalyst could be used.

Another important approach has involved developing heterogeneous enantioselective catalysts for synthesis of chiral molecules for pharmaceuticals. Most effort here has been on immobilizing chiral homogeneous catalysts on solid supports, as reported in *Supported Catalysts and Their Applications*, (Royal Society of Chemistry 2001, pp. 38-47). Methods of immobilizing the catalytic species to the surface include covalent bonding. Heterogenization of chiral rhodium complexes of 1,2-diphosphines, already known to be active for enantioselective hydrogenation, has been achieved using the amine functionality of the pyrrolidine group in the rhodium complex of 3,4-(R,R)-bis(diphenylphosphino)pyrrolidine. Various linker groups were used to attach the pyrrolidine to the silica surface, including —C(O)C(O)—, —C(O)$C_6H_4$C(O)—, —C(O)(CH$_2$)$_3$C(O)—. The immobilized complex was found to catalyze the hydrogenation of α-(acetylamino)cinnamic acid and its methyl ester, with very high enantioselectivity (>90%). Chiral complexes of Rh(I), Ru(II), Co(II) and Ni(II) based on β-aminoalcohols such as L-prolinol have also been anchored onto silica and modified USY-zeolites to perform the similar enantiomeric hydrogenation reactions. Another method of preparing chiral heterogenized catalysts uses sol-gel chemistry. Co-hydrolysis of substituted alkoxysilanes containing ligand, and ethyl silicates, followed by co-condensation has been used to generate supported homogeneous catalysts with a hybrid organic-inorganic solid where chiral organic species are attached to an inorganic silicate framework. Chiral moieties comprise such units as trans-diaminocyclohexane and binaphthyl. Rhodium complexes of such ligands are enantioselective catalysts for hydrogen transfer reduction of prochiral ketones to chiral alcohols. Chiral moieties have also been tethered onto the inner surface of zeolite MCM-41. After the exterior surface of the zeolite was deactivated, the inner walls were functionalised with a chiral ligand 3-{(S)-1-[(R)-1',2-bisdiphenylphosphino)ferrocenyl]ethyl-N,N'-dimethylethylenediamino}propylsilane chains. Reaction with PdCl$_2$ gave a mesoporous chiral catalyst with higher regioselectivity and enantioselectivity in the Trost-Tsuji amination reaction than the same catalytic site tethered to high surface area silica. Enantioselective epoxidation reactions have also been reported using immobilised Sharpless tartrate-titanium isopropoxide or Jacobsen-Katstuki complexes on polymers. Other routes to immobilized enantioselective epoxidation catalysts include ion exchange of Al-MCM-41 with manganese and cobalt cations and subsequent modification of the metal centre by a chiral salen ligand. In both cases the immobilised complexes are similar or better than the homogeneous complexes in terms of reactivity and enantioselectivity. The "Ship in a Bottle" approach has also been used to immobilise organometallic complexes within the pores of zeolites where leaching is prevented by the restrictive pore openings. (Salen)-manganese and -cobalt complexes have been used for the stereoselective epoxidation of olefins using large pore zeolites such as zeolite-Y. For the epoxidation of (−)alpha-pinene with oxygen/pivalic aldehyde at room temperature, an immobilised Co(salen-5) complex achieved 100% conversion, 96% selectivity and 91% diasteromeric excess, superior to the homogeneous counterpart. The catalyst is reusable and does not leach (reported in *Supported Catalysts and Their Applications*, Royal Society of Chemistry, 2001, pp 82-86).

Another important approach has involved developing immobilized base catalysts, for catalysis of a wide range of base-directed reactions such as Michael additions, esterifications and transesterifications. Such bases reported to have been immobilized include guanidines and biguanides. Guanidines have been tethered to silica using trimethoxysilyl-propyl and glycidol tethers; and to zeolite MCM-41, first grafting the surface with the chlorosilane followed by amination with a bicyclic guanidine. These catalysts are active for transesterifications of methyl acetate to ethyl acetate, ethyl propionate with butanol and in the Knoevenagel condensation of benzaldehyde with ethyl cyanoacetate. Tricyclic guanidines have been immobilised inside the pores of a zeolite and used as a trapped base for the aldolisation of acetone with benzaldehye to selectively produce the crotonisation product. Guanidines have also been grafted onto polymeric supports and shown to be active for transesterification reactions. The transesterification of vegetable oils requires even stronger bases and N-alkylated biguanides have been tethered to polystyrene and demonstrated in the transesterification of triglycerides from vegetable oils. Polystyrene bound biguanides exhibited excellent catalytic activity under the same conditions and immobilisation induced only a very limited decrease in activity. Yields above 94% were observed in less than 15 min. The yields of methyl esters were above 94% before 15 minutes. The use of guanidine catalysts supported on silica and micelle templated silicas have also been reported for the epoxidation of cyclohexanone. The use of amine-silica materials supported on hexagonal mesoporous silica (HMS) prepared via an in-situ sol-gel method or grafting onto a pre-prepared HMS support has been investigated, for the Knoevenagel reaction between cyclohexanone and ethyl cyanoacetate (ECA). Both catalysts gave excellent selectivity to the desired product (reported in *Supported Catalysts and Their Applications*, Royal Society of Chemistry 2001, pp 203-213).

Yet another important approach has involved developing immobilized metal-complex catalysts for catalysis of carbonylation reactions, an ordinarily homogeneously-catalysed process used widely to produce acetic acid from methanol and carbon monoxide using soluble complexes of rhodium and iridium. Here again there has been an interest in heterogenizing the metal complexes onto a solid support to confine the catalyst to the reactor and eliminate the need for catalyst separation and recovery. Various solid supports have been used including carbon, inorganic oxides, zeolites and polymers. One method of attaching the complex involves covalent bonding of a pendant group of a ligand (usually a phosphine) to the carbon or polymer. However metal-ligand cleavage causes leaching of the metal and the acidic conditions can degrade the phosphine ligands. One way to overcome this is to anchor the complex by ionic interactions between ionic metal complexes and a polymeric ion exchange resin and there has been increased interest in this strategy using a polyvinylidene resin tolerant of elevated temperatures. One method for preparing such catalysts uses macroporous copolymers of vinylpyridine and styrene cross-linked with divinyl benzene as polymer supports for $[M(CO)_2I_2]^-$ where M=Rh or Ir; the anionic metal complex is loaded via an ion-exchange process.

Finally, oxidation of primary alcohols to aldehydes and secondary alcohols to ketones are key steps in organic synthesis. The use of stable nitroxyl radicals such as TEMPO for homogeneous catalytic oxidation of alcohols to aldehydes, ketones and carboxylic acids is well documented. Several immobilized heterogeneous TEMPO based catalysts have been reported using silica and MCM-41 as supports and hypochlorite as the oxidant. Recently, a polymer immobilized TEMPO has been reported, known as PIPO (Polyamine Immobilised Piperidinyl Oxyl) based on a commercially available Chimassorb 944. PIPO is more active than silica and MCM-41 supported TEMPO catalysts in the bleach-oxidation of octan-2-ol under chlorinated hydrocarbon solvent-free and bromide-free conditions and efficiently oxidises primary, secondary and benzylic alcohols. *Supported Catalysts and Their Applications* pp 118-124.

All of the above applications of "heterogenized" homogeneous catalysts for manufacturing fine chemicals or commodity chemicals would require their use in typical industrial scale reactors. Depending on the reaction, these include reactors with moving catalyst particles in suspension (stirred tank, bubble column, jet loops, fluidised beds, slurry) or reactors where the catalyst is fixed (trickle bed or 3-phase monolith reactors). Stirred tank, bubble column, fluidized beds, jet loops and slurry reactors operating in batch or semi-continuous all have the disadvantage of requiring very fine catalyst particles so that they stay in suspension, but which are difficult to separate from the products. These reactors also suffer from homogeneous side reactions leading to loss of selectivity. Trickle bed reactors have the catalyst bed fixed so that additional separation of the catalyst from the products is not required but the relatively large catalyst particles required to minimize pressure drop leads to a loss of catalyst effectiveness, poor heat transfer, and inefficient scale-up. Three-phase monolith reactors have adequate mass transfer properties but heat transfer is poor and uniform distribution of reactants throughout the channels of the monolith is difficult.

Despite extensive work in immobilized, ordinarily homogeneous catalysts, there remains a need to develop heterogeneous catalysts combined with reactor systems which together exhibit good heat and mass transfer, excellent control of temperature and residence time, with high selectivity, minimization of by-products, low pressure drops and high efficiency of separation from reactants.

SUMMARY OF THE INVENTION

The invention provides a catalytic system comprising microchannel reactor containing a tethered catalyst composition in a microchannel of the reactor. In one embodiment, the catalyst composition defines at least one wall of a bulk flow path. In this embodiment it is advantageous that there be provided at least one heat transfer microchannel adjacent said at least one wall of a microchannel. Alternatively, the catalyst composition is provided as, or part of, a porous insert. Such porous insert can be adjacent to at least one wall of a microchannel of said reactor, and there can be provided at least one heat transfer microchannel adjacent the wall. The tethered catalyst composition can comprise a solid support, such as one or more of solid inorganic oxide, carbon, polymer, silica, alumina, clay, zeolite or mesoporous solids e.g. MCM-41 and SAMMS (see publications of Jun Liu et al. and others for descriptions of this well known class of materials). The tethered catalyst comprises a catalyst or procatalyst moiety which is ordinarily homogeneous. Preferably, this moiety contains or is a metal coordination complex, organometallic complex, enzyme, oxidant, reductant, acid, and/or base. This catalyst system can be further characterized by either (1) superior heat and/or mass transfer characteristics, and/or (2) superior control of temperature and residence time, and/or (3) superior selectivity and minimization of by-products and/or (4) less catalyst attrition, all of these being realized when the catalyst is used within a microchannel reactor.

The invention also discloses methods for catalytic chemical conversion, such method comprising flowing a reactant fluid mixture into a microchannel, wherein a tethered catalyst composition is present in the microchannel, and reacting the reactant fluid mixture into desired products in the microchannel. This method further comprehends a catalytic conversion of the reactant fluid mixture into desired products. Such catalytic conversions can include, but are not limited to: hydrogenation, dehydrogenation, hydrogenolysis, hydroformylation, hydrosilation, oxidation, reduction, isomerization, aromatization, hydrocyanation, olefin metathesis, carbonylation, decarbonylation, carboxylation, epoxidation, oxygen insertion reactions, oxidation of alcohols to carbonyls and carboxylic acids, olefin polymerization, oxygen transfer, hydrogen transfer, hydrogenation of imines, nitrogen transfer, Heck Reaction, alkylation, amination, cyclopropanation, addition reactions (e.g., Michael addition), condensation (e.g., Knoevenagel condensation), hydration, dihydroxylation of olefins, dehydration, Suzuki reaction, Buchwald-Hartig Reaction, Sonogashira Reaction, cross coupling reactions, and esterification. These conversions can be made to be enantioselective and/or diastereoselective through appropriate choice of tethered catalyst composition. Depending on reaction conditions, catalytic conversions can be run with reactants (and/or products) in the vapor phase, liquid phase or a mixed vapor-liquid phase. Conditions are selected such that a reaction will occur to form one or more product. These inventive methods can be further characterized by either (1) superior heat and/or mass transfer characteristics, and/or (2) superior control of temperature and residence time, and/or (3) superior selectivity, yield, and/or minimization of by-products, and/or (4) cooling the microchannel by flowing a coolant through an adjacent cooling chamber, and/or (5) quenching the reactant stream. For some reactions, better control over temperature and residence time allows use of higher temperatures that increase reaction rates but still retains high selectivity—this in turn allows reactions to be completed in much less time than normal, e.g. minutes vs hours. Rapid heat up and mixing of reactants using micromixers, microchannel preheaters (containing no catalyst) followed by rapid cooling using microchannel heat exchangers (again containing no catalyst) can ensure accurate control over temperature and residence time at the desired temperature and in the presence of catalyst. It has been found with some tethered catalysts that isolation and reuse deactivates the catalyst. Thus, the inventive systems are superior to batch reactors because the catalyst need not be exposed to cyclic conditions. Furthermore, a tethered catalyst can be deactivated in regions of a reactor that have slow or stationary flow. Thus, the inventive systems are superior to conventional batch or continuous-flow reactors because microchannel reactors can be designed to have uniform flow to all regions of a reaction chamber.

Preferred embodiments of the process of the present invention can be operated, if desired, under intensive conditions which lead to greater throughput. By combining catalytic microchannel and adjacent heat exchangers it is possible to operate at reactant ratios that would conventionally lead to high temperatures and loss of selectivity, but by removing heat rapidly through heat exchange with the heat removal channels, the temperature in the catalytic channels can be kept at relatively low temperatures which are effective to optimize reaction selectivity. Preferred embodiments of the present invention permit reactions to be conducted at higher temperatures at much shorter contact times while reducing undesired side reactions.

In another aspect the invention provides systems or methods in which a tethered chiral auxiliary is present in a microchannel of a microchannel reactor. In one embodiment, the tethered chiral auxiliary is present on at least one wall of a microchannel at the border of a bulk flow path. The system design and operation is analogous to that described herein with respect to tethered catalysts except that the tethered catalyst is replaced by a tethered chiral auxiliary. Alternatively, a microchannel may contain both a tethered chiral auxiliary and a tethered catalyst. The discussions provided herein with respect to supports, conditions, etc. also apply to systems and methods containing a tethered chiral auxiliary. These systems and methods may be characterized by an enhanced stereoselectivity in the reaction of one or more reactants to form one or more chiral products.

The subject matter of the present invention is particularly pointed out and distinctly claimed in the concluding portion of this specification. However, both the organization and method of operation, together with further advantages and objects thereof, may best be understood by reference to the following description.

GLOSSARY OF TERMS USED

As used herein, a tethered catalyst composition refers to a heterogeneous catalytic system containing a solid support onto which has been immobilized an otherwise ordinarily homogeneous catalyst or procatalyst moiety. The tethered (ordinarily homogeneous) catalyst includes catalysts that have a ligand or ligands replaced by a covalent bond and/or a linking moiety to a support. A heterogeneous catalytic system is present as a separate phase from at least one of the reactants undergoing chemical conversion in a catalytic reaction. Immobilized refers to a state of attachment to a solid support via one or more covalent bond(s), either directly or indirectly through a linking moiety; or via ionic forces. Procatalyst refers to a moiety which may not per se act as a catalyst but which is converted into a catalytically active species during suitable reaction conditions. An ordinarily homogeneous catalyst or procatalyst moiety is one which would be present in the same phase as at least one of the reactants undergoing catalytic conversion, but for the state of being immobilized.

A "chiral auxiliary" is an asymmetric molecule which biases a reaction to favor selective formation of one stereoisomer over another.

DESCRIPTION OF THE INVENTION

Figure 1:
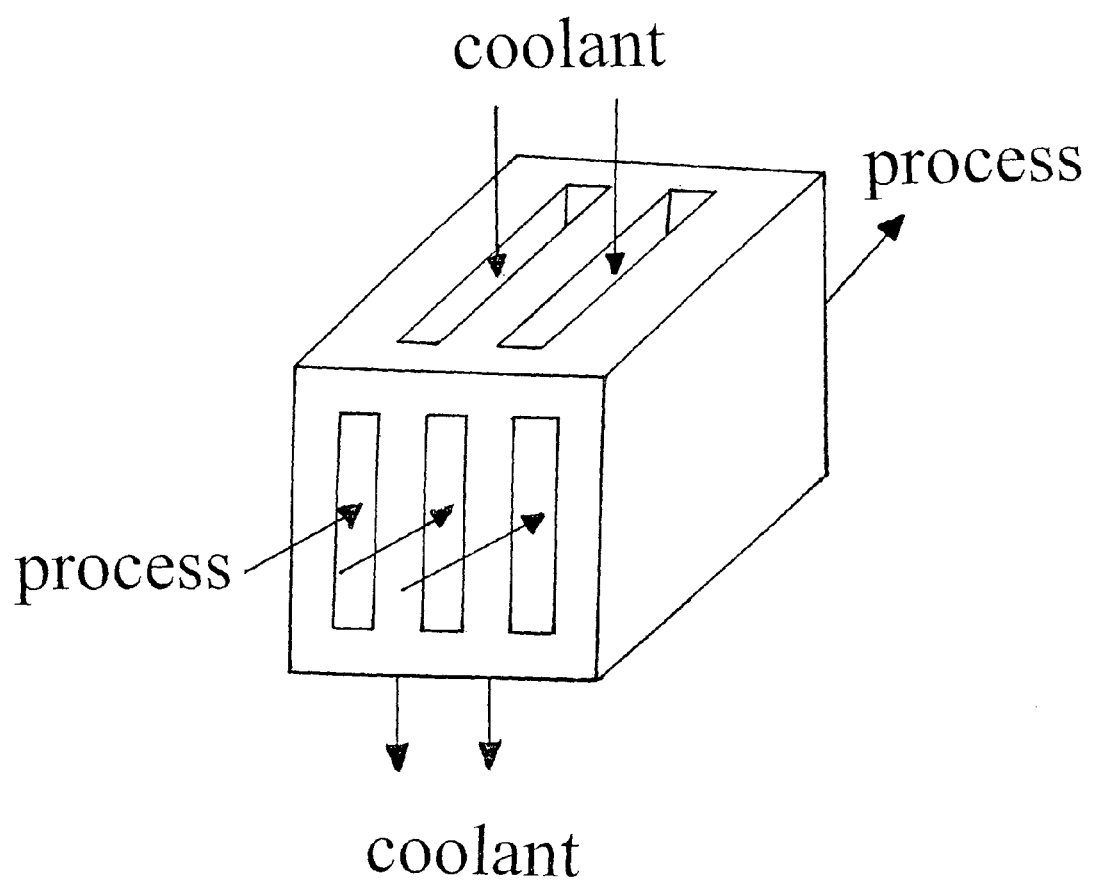
FIG. 1 is a schematic and simplified view of a microchannel reactor in which reactant feed passes through a reaction microchannel (side) while coolant (in a cross-flow arrangement) flows through an adjacent heat exchanger (top).

The invention includes a catalytic system comprising microchannel reactor containing a tethered catalyst composition, in particular, one in which the tethered catalyst composition is present in a microchannel. Microchannel reactors are characterized by the presence of at least one reaction channel having at least one dimension (wall-to-wall, not counting catalyst) of 5 mm or less, preferably 2.0 mm or less (more preferably about 1.0 mm or less) and greater than 100 nm (preferably greater than 1 µm), and in some embodiments 50 to 500 µm. Both height and width are substantially perpendicular to the direction of flow of reactants through the reactor. Microchannels are also defined by the presence of at least one inlet that is distinct from at least one outlet—microchannels are not merely channels through zeolites or mesoporous materials. The height and/or width of the reaction microchannel is preferably about 2 mm or less, and more preferably 1 mm or less (in which case the reaction chamber falls within the classical definition of a microchannel). The length of the reaction channel is typically longer. Preferably, the length of the reaction channel is greater than about 1 cm, more preferably in the range of about 1 to 2 m, and in some preferred embodiments 1 to 20 cm. Microchannels can be lengthened by a serpentine configuration and/or by flow paths that continue over multiple layers, for example a channel a conduit can connect a channel in one layer to a channel in another layer. In some embodiments, flow from a microchannel reactor can be recycled back into the same or a different microchannel reactor for further reaction. FIG. 1 illustrates one possible configuration for a microchannel reactor. This illustrated example uses interleaved microchannels for cooling; however, other embodiments can operate with heating, or without heat exchange, etc.

The sides of the reaction channel are defined by reaction channel walls. These walls are preferably made of a hard material such as a ceramic, an iron based alloy such as steel, or monel. The choice of material for the walls of the reaction channel depend on the reaction. In some embodiments, the reaction chamber walls are comprised of a stainless steel or inconel which is durable and has good thermal conductivity. Some reactions will require materials that resist acid or base conditions. In embodiments that do not require high temperatures or high thermal conductivities, plastic may be a preferred material for the construction of the microchannel. The reactors can be made by known methods, and in some preferred embodiments are made by laminating interleaved plates (also known as "shims"), and preferably where shims designed for reaction channels are interleaved with shims designed for heat exchange.

The reactors preferably include a plurality of microchannel reaction channels and/or a plurality of adjacent heat exchange microchannels. The plurality of microchannel reaction channels may contain, for example, 2, 10, 100, 1000 or more channels. In preferred embodiments, the microchannels are arranged in parallel arrays of planar microchannels, for example, at least 3 arrays of planar microchannels. In some preferred embodiments, multiple microchannel inlets are connected to a common header and/or multiple microchannel outlets are connected to a common footer. During operation, the heat exchange microchannels (if present) contain flowing heating and/or cooling fluids. Non-limiting examples of this type of known reactor usable in the present invention include those of the microcomponent sheet architecture variety (for example, a laminate with microchannels) exemplified in U.S. Pat. Nos. 6,200,536 and 6,219,973 (both of which are hereby incorporated by reference). Performance advantages in the use of this type of reactor architecture for the purposes of the present invention include their relatively large heat and mass transfer rates, and the substantial absence of any explosive limits. Unlike conventional reaction vessels for catalytic conversion, (such as reactors with moving catalyst particles in suspension, e.g., stirred tank, bubble column, jet loops, fluidized beds, slurry; or conventional reactors where the catalyst is fixed, e.g., trickle bed or 3-phase monolith reactors), microchannel reactors combine all the benefits of good heat and mass transfer, excellent control of temperature, residence time and minimization of by-products. Pressure drops are low, allowing high throughput and the catalyst is fixed in a very accessible form within the channels eliminating the need for separation. Furthermore, use of microchannel reactors can achieve better temperature control, and maintain a relatively more isothermal profile, compared to architectures of the prior art. This, in turn, advantageously leads to lessened peak temperatures and lessened side reactions. The reduced residence time also reduces the extent of undesired side reactions.

In some embodiments, the reaction microchannel (or microchannels) contains a bulk flow path. The term "bulk flow path" refers to an open path (contiguous bulk flow region) within the reaction chamber. A contiguous bulk flow region allows rapid fluid flow through the reaction chamber without large pressure drops. In some preferred embodiments there is laminar flow in the bulk flow region. Bulk flow regions within each reaction channel preferably have a cross-sectional area of $5\times10^{-8}$ to $1\times10^{-2}$ m$^2$, more preferably $5\times10^{-7}$ to $1\times10^{-4}$ m$^2$. The bulk flow regions preferably comprise at least 5%, more preferably at least 50% and in some embodiments, 30-80% of either 1) the internal volume of the reaction chamber, or 2) the cross-section of the reaction channel.

In addition to the reaction microchannel(s), additional features such as microchannel or non-microchannel heat exchangers may be present. Microchannel heat exchangers are preferred. An integrated or separate heat exchanger can be used to quench reaction products of the catalytic conversion, cooling them down rapidly once the reaction has taken place to prevent further undesirable reactions. In some embodiments of the inventive reactor or method, the reactor (or method) is configured to send the product stream into a second reactor or recycle the product stream back into the same reactor. Adjacent heat transfer microchannels enable temperature in the reaction channel to be controlled to promote selective reactions and minimize unselective reactions that increase with temperature. Heat exchange fluids may flow through adjacent heat transfer microchannels, and can be gases or liquids and may include steam, liquid metals, or any other known heat exchange fluids—the system can be optimized to have a phase change in the heat exchanger. In some preferred embodiments, multiple heat exchange layers are interleaved with multiple reaction microchannels (for example, at least 10 heat exchangers interleaved with at least 10 reaction microchannels.

The tethered catalyst can take the form of a catalyst material coated on a monolithic insert, a coating, or, less preferably, particles or a powder. The tethered catalyst can be supported on the wall (or portion of a wall) of a reaction microchannel or tethered directly to the wall. The tethered catalyst could also be supported on a monolithic insert or on powders or particles. Preferred catalyst monolithic insert materials include felts (nonwoven fibers or strands), foams, screens gauzes and foils. The insert can have the advantage of being conveniently removable from a reactor. Preferably the tethered catalyst is on or adjacent to at least one microchannel wall of a reactor, and there is a heat exchanger adjacent that wall. Examples of support material for the tethered catalyst include one or more of solid inorganic oxide, carbon, polymer, silica, alumina, clay, zeolite and/or mesoporous solid e.g. MCM-41. Representative further examples of such solid inorganic oxide including titania, zirconia, hafnia, magnesia, tin oxide, chromium oxide and oxides of other metals and metalloids. A linker group, as known in the prior art, can link the support with a catalyst or procatalyst moiety which is ordinarily homogeneous.

Figure 2:
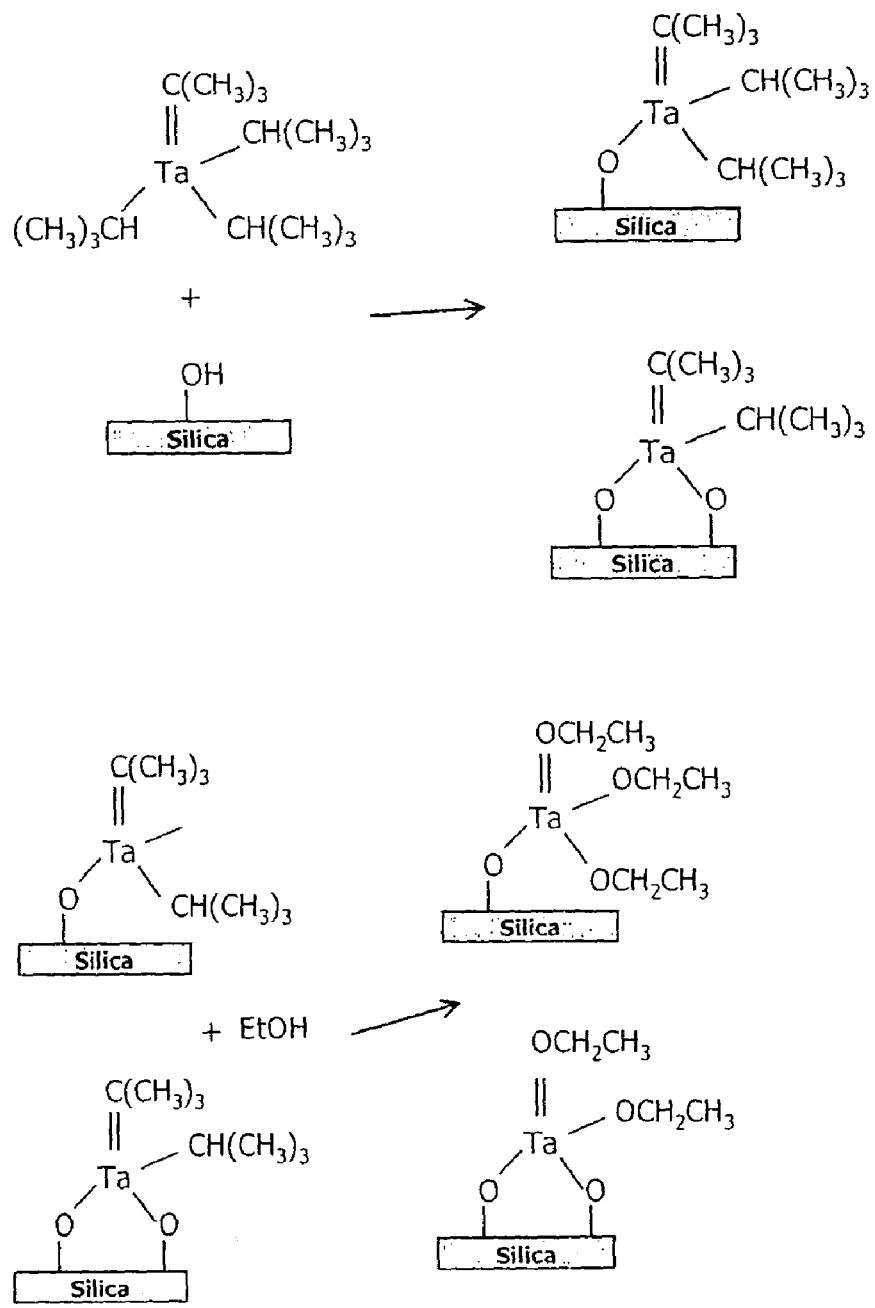
FIG. 2 illustrates one mechanism for tethering a catalyst.

Numerous types of tethers can be used in the present invention. For example, there can be covalent bonding of metal complexes onto hydroxyl groups on inorganic supports such as silica, alumina, zeolites, clays, mesoporous silica, aluminosilicates, titania, etc. In some preferred embodiments, the tether is between 2 and 9 atoms long and, in some embodiments, preferably the tether contains at least one, in some embodiments, at least two, carbon atoms. In some cases a tether such as 3-chloropropylsilane ($Cl-CH_2-CH_2-CH_2-SiH_3$) (or chloropropyl trimethoxysilane, $Cl-CH_2-CH_2-CH_2-Si(OCH_3)_3$ or $Cl-CH_2-CH_2-CH_2-NH_2$) is reacted with the support surface and the resulting modified surface reacted with a metal complex or complexes. Alternatively, the metal complex could be first reacted with a tether (forming, for example, a metal-attached $-CH_2-CH_2-CH_2-SiH_3$ group) that is subsequently reacted with an inorganic support. Similarly, metal complexes can by prepared with ligands capable of tethering with a surface. For example, palladium catalysts in the form of palladacycles may be tethered to polymeric supports such as polystyrene, poly(ethylene glycol) and oxide supports such as silica. Another tether can be a bridging oxo group connecting a transition metal center of a tethered catalyst with a surface metal or semimetal. Preferably, an oxo bridge is formed by reaction of an organometallic compound with a surface; one example is illustrated in FIG. 2. This tethered catalyst is known for asymmetric epoxidations. See Song, C. E., Lee, S., 'Supported Catalyst on Inorganic Materials', *Chem. Rev.*, v102 p 3495-3524, 2002.

In some preferred embodiments, the tether contains at least a three atom long chain connecting a metal center with a surface oxygen. In another preferred embodiment, a tethered chiral auxiliary, such as ephedrine, can be used, for example, with an alkyl zinc reagent to convert aldehydes to chiral alcohols. Other surface groups, such as a surface amino group can be used to bind a tethered catalyst, see, for example, U.S. Pat. No. 6,040,261, incorporated herein by reference. Catalysts can also be made by tethering to a phosphinated polymeric support, for example reacting a polymer supported diphenylphosphine with a metal CO complex.

Metal ions can be ionically exchanged onto inorganic surfaces and then reacted with ligands to forms catalytic species.

Lewis acids can be chemically tethered by chemisorption of $AlCl_3$, $SbF_3$, zinc triflate, aluminum alkyls, etc. where the Lewis Acid reacts directly with surface hydroxyls to form a convalently tethered Lewis Acid catalyst. Tethered can also be prepared from ionic liquids grafted onto a support for example a complex of an organic cation such as an imidazolium cation combined with an inorganic anion such as $AlCl_4^-$.

Tethered catalysts can also be prepared by a ship-in-bottle approach whereby the catalyst is assembled inside large cavities inside the support, the support having access pores smaller than the size of the catalytic complex such that the catalyst is effectively trapped inside the support. See, for example, Ogubwumi et al. Chem. Comm. p 901, 1997 and Sabater et al. Chem. Comm. p 1285, 1997.

Catalysts can also be tethered to surfaces via phosphine-containing tethers, see, for example, U.S. Pat. No. 5,252,751 incorporated herein by reference, and GB 1 552 018.

The catalysts can also be tethered bases, for example base catalysts such as amine groups can be tethered to surfaces using 3-aminopropyltrimethoxysilane (AMPS), 3-aminopropyltriethoxysilane, N,N-dimethylpropylaminotrimethoxysilane and similar compounds having a basic group at one end and an oxygenated group at the other to tether to the surface via surface hydroxyl groups. Guanidine can be alkylated with 3-chloropropyltrimethoxysilane (or 3-glycidyloxy)propyl)trimethoxysilane) and reacted with surface hydroxyls to tether the base via the Si group. Alternatively, bases can be tethered to polymer supports such as with omega-chloroalkylpolystyrenes to form a tethered catalyst having the formula polystyrene-$C_6H_4-(CH_2)$n-guanidine base.

Tethered metallocenes can be formed by including on at least one of the cyclopentadiene ligands substituents that can react with surface hydroxyls to tether the metallocene for oligomerization, polymerization or hydrogenation reactions. Substituents may include propylsilane or propylsiloxy groups or longer alkyl or aralkyl chains, for example substituents such as $-CH_2-CH_2-CH_2-SiH_3$, $-CH_2-CH_2-CH_2-Si(OEt)_3$, or $-CH_2-(CH_2)_n-SiR_3$. wherein R is any combination of alkoxys, amines and hydrogens and n is 1 to 10.

The tethered catalyst comprises a catalyst or procatalyst moiety which is ordinarily homogeneous, such moiety containing or being, inter alia, a metal coordination complex, organometallic complex, enzyme, oxidant, reductant, acid, and/or base. For example the catalyst or procatalyst moiety can contain metal coordination complexes of groups 2-11 of the periodic table of the elements, the lanthanides, and actinides. Some of the more commonly employed metals can be Ti, V, Cr, Mn, Fe, Co, Ni, Zr, Mo, Re, Ru, Rh, Pd, Pt, Ta, Os, Ir, Zn and Cd, but any of the other transition metals, lanthanides, or actinides can be used. Non-transition elements can also be comprises by the tethered catalyst compositions of the invention. Some well known organometallics catalysts/procatalysts which have heretofore been used as homogeneous catalysts and which are susceptible of tethering for use in the instant invention include, but are not limited to: $Ni[P(OMe)_3]_4$, $RhCl_3(SR_2)_3$, $NiCl_2(PEt_3)_2$, $RhH(CO)(PPh_3)_3$, $RhCl(CO)(PPh_3)_2$, $IrCl(CO)(PPh_3)_2$.

Schiff base palladium catalysts suitable for Heck and Suzuki coupling reactions can be prepared by modification of the coated aluminium surface with aminopropyl tetheres that are subsequently converted to the Schiff base via condensation with 2-pyridine carbaldehyde. Complexation using palladium acetate in acetone produces the active Pd catalyst.

A tethered catalyst can also have a dendriditic morphology. Examples of dendrimers include: amine dendrimers, silane dendrimers, polybenzyl ether dendrimers, carboxyl benzyl amine dendrimers, phenylacetylene denrimers, and poly(amido amine) dendrimers. Dendrimer catalysts have been described by van Heerbeek, R., Kamer, P. C. J., van Leeuwen, P. W., Reek, Joost, N., in 'Dendrimers as Support for Recoverable Catalysts and Reagents', *Chem. Rev.*, v102 p 3717-3756, 2002. Preferably, a dendritic tether has more attachments to catalyst catalyst centers that to the substrate; for example, a single attachment to a substrate connecting to multiple catalyst centers.

Non-transition elements and their compounds can also be used including, but not limited to, amines and aluminum alkyls. Enzymes can also be tethered in the instant invention, such enzymes including but not limited to glucose isomerase and tyrosinase. These examples are included for their illustrative value, but are not intended to limit the invention. The tethered catalyst could be any of the tethered catalysts mentioned in the Introduction section. Other examples of tethered catalyst compositions usable in the present invention are disclosed in the following U.S. Patents, all of which are hereby incorporated by reference: U.S. Pat. No. 3,816,340; U.S. Pat. No. 5,789,333; U.S. Pat. No. 6,136,746; U.S. Pat. No. 6,025,295; U.S. Pat. No. 6,005,148; U.S. Pat. No. 6,040,261; U.S. Pat. No. 6,087,293; U.S. Pat. No. 6,331,601; U.S. Pat. No. 6,194,343; U.S. Pat. No. 6,455,458; and U.S. Pat. No. 4,276,195. These patents are incorporated both for their descriptions of tethered catalysts and reactions that can be catalyzed by tethered catalysts. Additional patents that are incorporated by reference herein both for their descriptions of tethered catalysts and reactions that can be catalyzed by tethered catalysts, include: U.S. Pat. No. 5,294,578 which discloses lewis acids anchored on the surface for the catalysis of conversions such as Friedel-Crafts type reactions, olefin oligomerization, aromatic alkylation, alkane alkylation and isomerization reactions; U.S. Pat. No. 5,326,920 which describes the polymerization of isobutene over a tethered catalyst; U.S. Pat. No. 5,451,704 which describes a process of producing lubricant basestock over a tethered catalyst; and U.S. Pat. No. 5,789,333 which describes the use of a tethered catalyst in the presence of a second heterogeneous catalyst.

The tethered catalyst composition can define at least a portion of a bulk flow path through a microchannel. In some preferred embodiments, the inventive system (or method) includes a porous catalyst material containing a tethered catalyst composition on its surface. The porous catalyst has a length, a width and a thickness, and the porous catalyst defines at least a portion of at least one wall of a bulk flow path. In some preferred embodiments, the surface of the catalyst defines at least one wall of a bulk flow path through which the mixture passes. During operation, reactant mixture flows through the microchannel, past and in contact with the porous catalyst. In some preferred embodiments, the porous catalyst is provided as a porous insert that can be inserted into (or removed from) each channel in a single piece; preferably the porous insert is sized to fit within a microchannel with a width of less than 2 mm. In some embodiments, the porous catalyst occupies at least 60%, in some embodiments at least 90%, of a cross-sectional area of a microchannel. Alternatively, the catalyst can be provided as a coating (such as a washcoat) of material within a microchannel reaction channel or channels. The use of a flow-by catalyst configuration can create an advantageous capacity/pressure drop relationship. In a flow-by catalyst configuration, fluid preferably flows in a 0.1-1.0 mm gap adjacent to a porous insert or a thin layer of catalyst (such as a catalyst tethered to a washcoat) that contacts the microchannel wall (preferably the microchannel wall that contacts the catalyst is in direct thermal contact with a heat exchanger, preferably a coolant stream contacts the opposite side of the wall that contacts the catalyst).

At a point where the chamber height or the chamber width is about 2 mm or less, the chamber height and the chamber width define a cross-sectional area. In some preferred embodiments, the cross-sectional area comprises a porous catalyst material and an open area, where the porous catalyst material occupies 5% to 95% of the cross-sectional area and where the open area occupies 5% to 95% of the cross-sectional area. In some preferred embodiments, the open area in the cross-sectional area occupies a contiguous area of $5 \times 10^{-8}$ to $1 \times 10^{-2}$ $m^2$.

A "porous catalyst material" (or "porous catalyst") refers to a porous material having a pore volume of 5 to 98%, more preferably 30 to 95% of the total porous material's volume. At least 20% (more preferably at least 50%) of the material's pore volume is composed of pores in the size (diameter) range of 0.1 to 300 microns, more preferably 0.3 to 200 microns, and still more preferably 1 to 100 microns. Pore volume and pore size distribution are measured by Mercury porisimetry (assuming cylindrical geometry of the pores) and nitrogen adsorption. As is known, mercury porisimetry and nitrogen adsorption are complementary techniques with mercury porisimetry being more accurate for measuring large pore sizes (larger than 30 nm) and nitrogen adsorption more accurate for small pores (less than 50 nm). Pore sizes in the range of about 0.1 to 300 microns enable molecules to diffuse molecularly through the materials under most gas phase catalysis conditions. The porous material can itself be a catalyst, but more preferably the porous material comprises a metal, ceramic or composite support having a layer or layers of a catalyst material or materials deposited thereon. The porosity can be geometrically regular as in a honeycomb or parallel pore structure, or porosity may be geometrically tortuous or random. The catalyst layers, if present, are preferably also porous. The average pore size (volume average) of the catalyst layer(s) is preferably smaller than the average pore size of the support. The average pore sizes in the catalyst layer(s) disposed upon the support preferably ranges from $10^{-9}$ m to $10^{-7}$ m as measured by $N_2$ adsorption with BET method. More preferably, at least 50 volume % of the total pore volume is composed of pores in the size range of $10^{-9}$ m to $10^{-7}$ m in diameter.

Tethered catalysts can be prepared by known methods (or modifications of known methods) on supports such as powders, porous monoliths, beads, and particles. Then, the catalysts can be placed in a microchannel. Alternatively, the tethered catalysts can be applied to interior surfaces of a microchannel by techniques such as wash-coating and chemical vapor deposition. In this alternative, the catalyst is typically applied into an assembled microchannel apparatus; however, it is also possible to apply a tethered catalyst to a shim or shims and then bond the shim or shims under conditions that do not destroy the catalyst (such as by an adhesive and/or clamping shims together).

The invention also discloses methods for catalytic chemical conversion, such method comprising flowing a reactant fluid mixture into a microchannel, wherein a tethered catalyst composition is present in the microchannel, and reacting the reactant into desired products in the microchannel. This method further comprehends a catalytic conversion of the reactant fluid mixture into desired products. Such catalytic conversions can include, but are not limited to: hydrogenation, dehydrogenation, hydrogenolysis, hydroformylation, hydrosilation, oxidation, reduction, isomerization, aromatization, hydrocyanation, olefin metathesis, carbonylation, decarbonylation, carboxylation, epoxidation, oxygen insertion reactions, oxidation of alcohols to carbonyls and carboxylic acids, olefin polymerization, oxygen transfer, hydrogen transfer, hydrogenation of imines, nitrogen transfer, Heck Reaction, alkylation, amination, cyclopropanation, addition reactions, condensation, hydration, dihydroxylation of olefins, dehydration, Suzuki reaction, Buchwald-Hartig Reaction, Sonogashira Reaction, cross coupling reactions, and esterification. These conversions can be made to be enantioselective and/or diasteroselective through appropriate choice of tethered catalyst composition. Such catalytic conversions can be run in either the vapor phase or in solution or in a mixed vapor-liquid phase. These methods can be further characterized by either (1) superior heat and/or mass transfer characteristics, or (2) superior control of temperature and residence time, or (3) superior selectivity, yield, and/or minimization of by-products, or (4) cooling the microchannel by flowing a coolant through an adjacent cooling chamber, or (5) quenching the reactant stream.

An analysis has been conducted showing capture number "isobars" as a function of residence time and characteristic dimension. Capture number is the number of times a reactant molecule entering in the center of a reactant stream contacts the catalyst surface (assuming no reaction). Characteristic dimension is the diffusional distance (for a tube with catalyst on the interior walls the characteristic dimension is the internal radius). The cell used in the Examples would have a capture number of 100 at a residence time of 3500 s in a liquid having a $D_{eff}$ of $3.3 \times 10^{-5}$ cm$^2$/s, and a characteristic dimension of 0.7 mm. The cell would have a capture number of 15 at a residence time of 3500 s in a liquid having a $D_{eff}$ of $0.5 \times 10^{-5}$ cm$^2$/s, and a characteristic dimension of 0.7 mm.

In the inventive methods, preferably, the residence time and characteristic dimension are controlled to achieve a capture number of 100 or less, in some embodiments 50 or less, in some embodiments 20 or less, and preferably at least 10. In some preferred embodiments, the reactions are carried out in a liquid medium with a diffusivity ($D_{eff}$) of at least $0.5 \times 10^{-6}$ cm$^2$/s, preferably $0.5 \times 10^{-5}$ cm$^2$/s to $3.5 \times 10^{-5}$ cm$^2$/s. Preferably, the catalyst is disposed on the wall of a microchannel reaction chamber with an open flow channel through the reaction chamber. Preferably, the catalyst includes a tethered catalyst (or tethered chiral auxiliary). Preferably, the method is carried out in a microchannel reaction chamber with a characteristic dimension of 2 mm or less, preferably 1 mm, and in some embodiments 0.5 mm or less, and typically at least 0.1 mm. Residence time is preferably 10,000 s or less, more preferably 5000 s or less, and in some embodiments, residence time is in the range of 100 to 5000 s.

Various embodiments of the inventive method use the apparatus and tethered catalysts described above. In some preferred embodiments, two or more reactant streams are mixed (such as by a microchannel mixer that is separate or integral with the reaction microchannel) prior to entering the reaction microchannel. Mixing is preferably conducted before reaction but can be conducted during reaction such as by a mixer disposed with a reaction microchannel. In some embodiments, a reactant is added at points along the length of the microchannel (distributed feed). In preferred embodiments, heat is added and/or removed to and/or from a heat exchanger.

In some preferred embodiments, a stream is rapidly quenched after reaction, preferably decreasing the temperature from reaction temperature to a temperature where the reaction is effectively stopped within 10 milliseconds (ms), more preferably 1 ms after reacting (that is, after passing through the reaction zone), and in some embodiments 1 ms to 500 ms, preferably 1 ms to 100 ms. Temperatures in reaction microchannels can be measured with thermocouples. Rapid quenching can be accomplished by highly efficient temperature transfer from an adjacent heat exchanger or interleaved heat exchangers or by rapid mixing of the reaction stream with a secondary, cooler gas stream.

Contemplated Representative Examples

Representative examples can establish superiority of specific classes of reactions as well as the general inventive concept of conducting chemical reactions in microchannels over a tethered catalyst. One type of apparatus for conducting representative examples comprises three sections: (1) a preheat section comprising a narrow cylindrical bore metal or fused silica tube immersed in a water bath or other heating device to raise the temperature of the reactants up to the desired reaction temperature, (2) a reaction section comprising a similar narrow bore tube (of microchannel dimensions) with a tethered catalyst coated on the inner walls and also immersed in a water bath or other heating device at reaction temperature, and (3) a quench section comprising a similar narrow bore tube in a low temperature bath to stop further reaction especially unselective reactions. For oxidation and reduction using gaseous $O_2$ or $H_2$, a micromixer can be used either prior to the preheat section or immediately after the preheat and before the reaction section. Alternatively, representative microchannel reactions can be run in testing apparatus having a microchannel with a rectangular cross-section—which could be made, for example, by machining the microchannel through a metal block. For better heat exchange, the apparatus can be machined to obtain thin walls in the direction of heat transport. In yet another alternative, for representative testing, the metal device can be placed in a tube and coolant flowed past the exterior of the device.

Superiority in Friedel Crafts type reactions can be shown by the alkylation of toluene with octene, or alkylation of benzene with dodecene, in a microchannel containing aluminum chloride tethered to a silica support (preferably with the silica or other support coated on the walls). In the benzene alkylation, a desired product would have the benzene ring at the 2 position on the olefin. For example, benzene can be alkylated with dodecene using an AlCl3 catalyst tethered to a support preferably silica coated on the wall of a microchannel reactor made of either fused silica or metal. Conventional supported catalysts in powder form and operated at room temperature in batch mode with excess benzene as the solvent can give yields of the linear alkyl benzenes (LABs) of up to 82% with 14% undesirable higher molecular weight products as a result of oligomerisation reactions. Reaction times are typically 1-2 hours depending on the excess of benzene used in the reaction, typically up to 10:1 benzene to dodecene necessary to limit doecene oligomerisation to heavies. A range of LAB isomers are formed with the 2 isomer (the most desired for biodegradability) typically 30% and the remainder being the less desirable 3, 4, 5 and 6 isomers. Turnover numbers for conventional supported catalysts are typically up to 150. In the microchannel reactor, the tethered catalyst can be operated at the same or higher temperatures up to 100° C., giving yields of LAB yields of over 90% with higher TONs (moles of product formed per mole of catalyst), for example greater than 200, in some instances 200 to 300, higher yields of the desired 2-isomer, for example 35 to 50%, and reduced yields of heavies which in turn prolongs catalyst lifetime. Lower excess benzene can also be used without increasing the yield of heavies formed in competing olefin oligomerization reactions.

Superiority in C—C bond formation, more specifically the Heck reaction, can be demonstrated by the reaction:

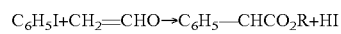

$C_6H_5I + CH_2{=}CHO \rightarrow C_6H_5{-}CHCO_2R + HI$

Triethylamine can be added to remove HI. Preferably this reaction is conducted over a tethered Pd complex, for example tethered to silica by amino linkages. The microchannel reactor permits operation at higher temperature and reduced residence times. For example, the Heck reaction of iodobenzene with methylacrylate using a Palladium catalyst tethered to a support such as silica coated on the walls of a microchannel reactor made of either fused silica or metal. Conventional supported powder catalysts in batch mode at 82° C., in acetonitrile solvent with an amine (IB:MA:Amine in 1:1:1 mole ratio) present to neutralize the HI generated suffer from low reaction rates. Typically conventional conversions are below 100% even after 10 hours and TONs are up to 2000. Using the tethered catalyst in the microchannel reactor operating at temperatures from 80 C. upwards (for example 82° C.) can have higher reaction rates and TONs. For example, conversions of at least 90% at residence times of less than 5 hours, in some embodiments 30 minutes to 2 hours, and, preferably, 30 minutes or less with TONs of 4000 or greater.

The same system can be used to demonstrate the superiority of the invention for Suzuki coupling reactions. Another reaction that can establish superiority in C—C bond formation, more specifically enantiomeric addition, is the reaction of diethyl zinc with benzaldehyde over a tethered chiral auxiliary catalyst to form a chiral alcohol. Preferably, enantioselectivity is at least 70%, more preferably at least 90%. For example, addition of diethylzinc to benzaldehyde using an AL-MTS-ephedrine (Aluminium-Mesoporous-Templated-Silica) tethered catalyst on the walls of a microchannel reactor made of either fused silica or metal. Typical conventional supported catalysts in batch mode and operating at 0° C., in diethyl ether as solvent and with 2.3 equivalents of diethylzinc have reaction rates of 0.2/hr requiring several hours to get high conversion. Selectivities to phenyl-propan-1-ol are typically below 95% with ee's up to 65%. The tethered catalyst in the microchannel reactor through better mixing, heat and mass transfer can give higher reaction rates, for example 0.3/hr or higher rates at 0° C., and higher rates at higher temperatures. in preferred embodiments, lower equivalents of diethylzinc, down to stoichiometric, can be used with no loss of reaction rate. In addition, ee is maintained or increased to over 70% while achieving the higher reaction rates and correspondingly lower reaction times.

Superiority in oligomerizations can be demonstrated by the oligomerization of a monomer such as methyl styrene to products with molecular weights in the range of 1000 to 4000 daltons, which could be used, for example, in adhesives. A preferred tethered catalyst can be based on boron trifluoride. Properties such as color and tackiness can be measured. Another exemplary reaction could be oligomerization of ethylene, propylene or butenes.

Superiority in reduction reactions, more specifically hydrogenations, or enantioselective reductions, can be demonstrated by the reduction of cinnamic acid using hydrogen gas to form a chiral product. In some preferred embodiments, flow is in a substantially Taylor flow regime with bubbles in the center and a thin liquid film at the microchannel walls to increase mass transfer to the catalyst. Preferably, in enantioselective reductions, enantioselectivity is at least 70%, more preferably at least 90%. For example, enantiomeric reduction of cinnamic acid can be conducted using a Rhodium catalyst tethered to a support, preferably silica coated on the wall of a microchannel reactor made of either fused silica or metal. Cinnamic acid is dissolved in methanol or a methanol/benzene mixture and fed into the microchannel reactor at room temperature. Hydrogen gas is co-fed at pressure using a micromixer or other device to generate very small bubbles or the hydrogen can be fed in Taylor flow whereby bubbles of hydrogen gas with a diameter approaching that of the microchannel, pass at regular intervals down the microchannel reactor creating a thin liquid film at the catalyst surface. Conventional supported catalysts in powder form, added at a level of 0.5 mole % Rhodium relative to the substrate, operating at room temperature and 50 bar pressure in batch mode typically produce yields of 100% after 70 hours with up to 70% ee (enantiomeric excess). Tethered catalysts in microchannel reactors operating at 50 bar hydrogen pressure and temperatures at and above room temperature, up to 200 degrees C., give 100% yield in less than 50 hours, preferably less than 10 hours, preferably less than 1 hour with higher ee, typically 75% and above. At higher temperatures (and higher reaction rates) the residence times are correspondingly lower. The tethered catalyst in microchannel reactor can also be operated at lower hydrogen pressure down to 1 bar especially in Taylor flow mode and still achieve acceptable reaction rates due to the much higher mass transfer in this mode of operation. Operation at higher temperatures in conventional batch systems leads to loss of selectivity and ee. Operation at lower hydrogen pressures in conventional systems leads to even lower reaction rates.

Superiority in oxidation can be demonstrated by oxidation of steroids using $(CH_3)_3COOH$ (tertbutyl hydroperoxide). Another reaction that can demonstrate superiority in oxidations is oxidation of alcohols to aldehydes, for example benzyl alcohol to benzaldehyde. The catalyst is preferably TPAP tethered to an inorganic support, such as silica or a mesoporous support such as MCM-41 or SAMMS. Another reaction that can demonstrate superiority in oxidations, specifically epoxidations, is epoxidation of terminal alkenes or styrene using Mn or Co chiral salen complexes tethered to Al-MCM-41. For example, benzyl alcohol can be oxidized to benzaldehye using a Rhuthenium catalyst tethered to a support, including for example silica as support with aminopropyltriethoxylsilane (AMPS) as the tether, with the support coated on the wall of a microchannel reactor made of fused silica or metal. Benzyl alcohol is dissolved in toluene and air or oxygen or oxygen enriched air is mixed into solution in the form of very small bubbles using a micromixer or in Taylor flow as described above. Conventional supported catalysts in powder form, with catalyst added at a level of 0.3 wt % Rhuthenium relative to the substrate and operated at 80 degrees C. give complete oxidation to benzaldehyde with high selectivity after 30 minutes reaction time with typical TONs of 300. The tethered catalyst in the microchannel reactor operated at 80 degrees C. and higher temperatures, up to 150 degrees C., gives increased TONs, for example at least 400, in some embodiments 400 to 1000, shorter reaction times than 30 minutes while maintaining selectivity to benzaldehyde.

Superiority of the general inventive concept can be shown by one or, more preferably several, representative examples.

EXAMPLES

Tethered Catalysts Examples

Experimental Details
Chemicals.
All chemicals were obtained from Aldrich and were used without further purification unless otherwise stated. Solvents used were reagent grade. All chemical reactions were carried out in normal atmospheric conditions and without efforts to degas or dry solvents.
Gas Chromatography.
Gas chromatography (GC) was undertaken on two machines. Knoevenagel reactions were monitored on a Shimadzu GC-17A Gas Chromatograph with a Shimadzu AOIC-20i Autosampler. Heck reactions and Michael reactions were analysed on a Varian 3800 Gas Chromatograph with a Varian 8200 Autosampler.

Example 1

The Knoevenagel Reaction

The Knoevenagel reaction[1] is a base catalyzed condensation reaction, typically between aldehydes and activated methylene compounds, and is one of the most important C—C bond forming reactions available to synthetic chemists. Usually catalyzed by strong bases such as sodium and potassium hydroxides and organic bases such as piperidine and pyridine in homogeneous reactions, the reaction is promoted by removal of water that drives the reaction equilibrium to the right. The use of solid catalysts has provided a simplification to the separation and purification of these reactions and catalysts such as basic zeolites[2] and amino-modified silicas[3] have been used. A recent communication reported the use of a multi-channelled membrane microreactor using Cs-exchanged faujasite NaX as the catalyst.[4]

The Knoevenagel reaction exemplified here was the condensation of benzaldehyde and ethyl cyanoacetate which forms α-cyanocinnamic acid ethyl ester, an intermediate in the production of an antihypertensive drug.

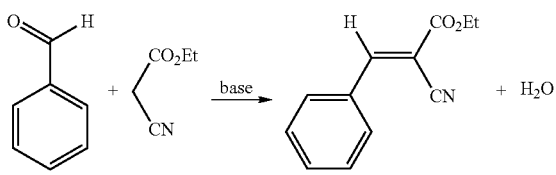

Preparation of the Tethered Base Catalyst

The tethered catalyst used here for the Knoevenagel reaction was based on a catalyst reported by Macquarrie et al. using aminopropyl supported on silica.[3] The catalyst was prepared by modification of silica coated inner surfaces of a microchannel flowcell reactor with 3-aminopropyltrimethoxysilane (AMPS) to tether the basic catalyst into the microchannel reactor.

Fabrication of the Microchannel Flowcell Reactor and Tethering the Knoevenagel Catalyst to the Reactor Surfaces.

Figure 3:
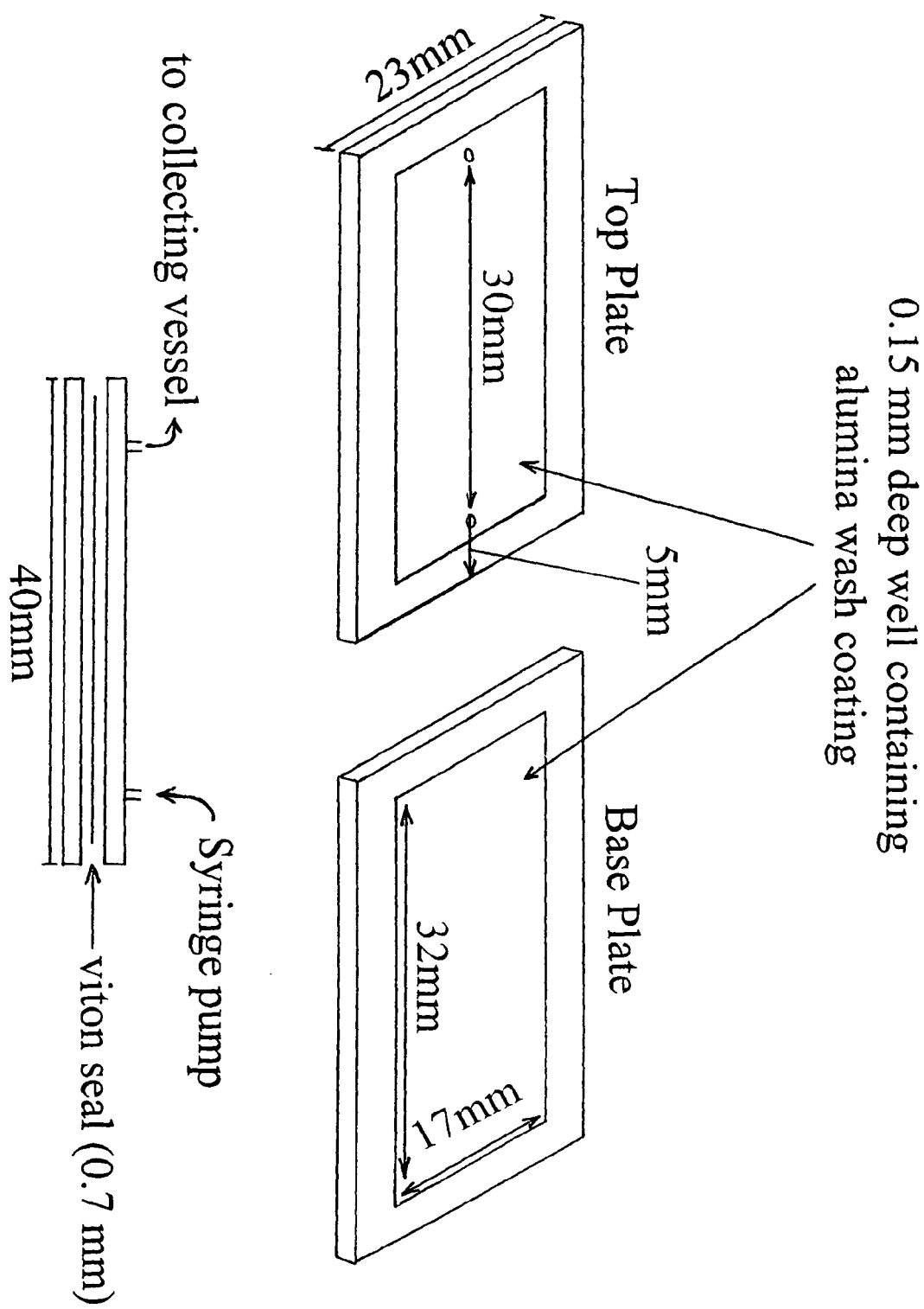
FIG. 3 illustrates the flow cell plates used in the Examples.

A pair of plates was machined out of a aluminium, one of the plates having drilled inlet and outlet holes (see FIG. 3).

Both plates had shallow wells 0.15 mm deep, in their surfaces. The aluminium surface was initially cleaned in toluene (30 min) before being removed, rinsed with toluene and dried in a vacuum oven (120° C.) for 1 h. The substrate was then placed in 2 M $NaOH_{(aq)}$ (30 min), rinsed with distilled water and acetone and then etched in conc. $HCl_{(aq)}$ for 30 secs (3×10 sec) and soaked in conc. $HNO_3$ for 5 min.

The 0.15 mm deep wells on each plate were then filled with sodium silicate (water glass) to which a couple of drops of 2 M $H_2SO_4$ was applied forming a gelatinous surface. The plates were then placed in an oven (200° C.) for 30 min. A thick layer of white solid formed on each surface, which was carefully removed until no further loose material remained. The treated surface showed a grey colored coating and a rough surface. The plates were soaked in water for 2 hours to remove excess sodium sulphate and then thoroughly rinsed. Weight gains on the 2 plates were 4 mg and 0.5 mg.

A solution of AMPS (10%) in dichloromethane was prepared and added dropwise to cover the silica coated plates. The plates were then placed in an oven (100° C.) for 15 min. This process was repeated a further two times. The plates were then soaked in methanol for 1 h which resulted in the removal of any excess AMPS. After drying, a weight gain of 2.9 mg and 1.7 mg was noted. Characterisation of the catalysts by Diffuse Reflectance Fourier Transform Infra Red (DRIFTS) gave definite evidence of aliphatic hydrocarbon and primary amine confirming the presence of the basic tethered catalyst.

Once derivatized, the plates were subsequently clamped together in an IR solution flow cell holder (Omni-cell body, Specac). The flow cell was sealed using a 0.7 mm thick viton gasket between the plates with viton washers of the same thickness sealing the inlet and outlet holes.

Knoevenagel Reaction Tests and Results.

Figure 4:
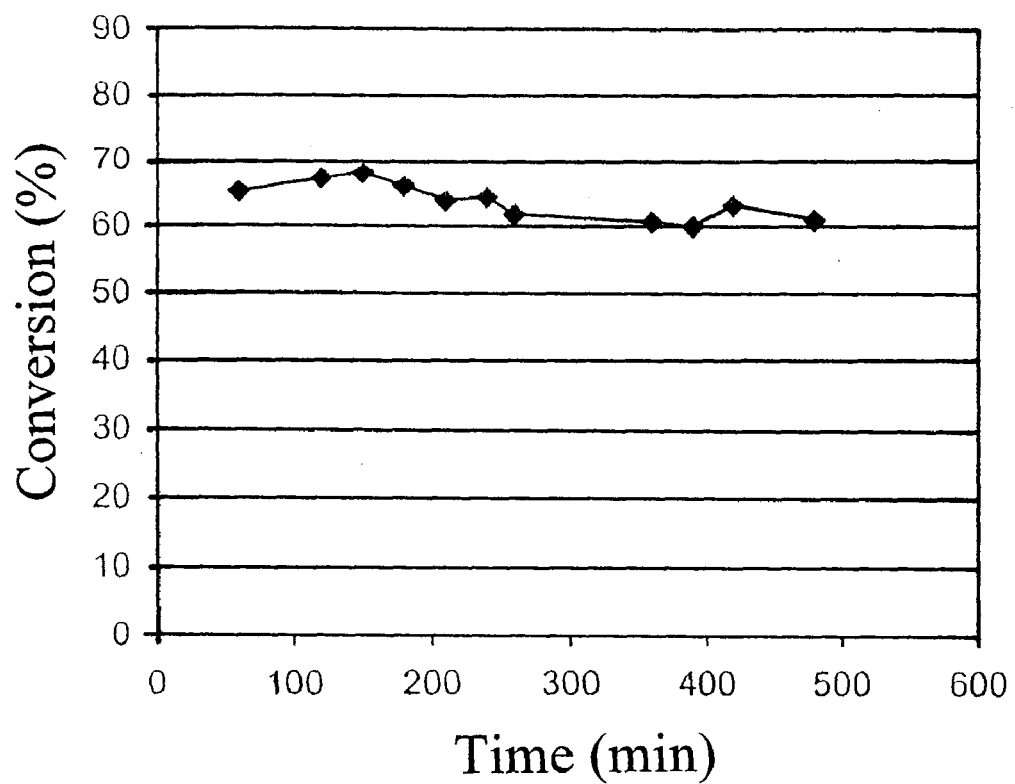
FIG. 4 is a graph of data showing the conversion of benzaldehyde over 8 hours of continuous flow at a residence time in testing of the Knoevenagel reaction through a microchannel.

A reaction mixture comprising of benzaldehyde (202 μL, 2 mmol), ethyl cyanoacetate (213 μL, 2 mmol) and 1,3-dibromobenzene (40 μL, internal GC standard) was prepared and injected into the flowcell (preheated to 90° C.) via a syringe pump at a flow rate of 6.6 μLmin$^{-1}$ corresponding to a residence time of 1 hour in the reactor. Conversions were measured each hour over a period of 8 hours of continuous flow. The results are shown in FIG. 4.

As can be seen from the graph, conversions remained relatively constant throughout at an average of over 60%. This can be compared with literature values for the same reaction at a slightly higher temperature using a conventional fixed bed reactor, a microreactor and a conventional base catalyst at much higher catalyst to reactor volume loadings[4]. In this report, the highest yield obtained from the fixed bed reactor is below 40% after 2 to 3 hours residence time. The yield in the fixed bed microreactor only reached 60% after 4 to 5 hours residence time.

Poisoning of heterogeneous primary amine base catalysts in Knoevenagel reactions has been previously reported as being ascribed to a slow reaction of the ester groups present in the reactant/product with the active centers of the catalyst. This process results in an in reversible loss in activity. On disassembly of the flowcell small patches of yellow discolouration were evident towards the corners of the plates. On analysis DRIFTS showed the yellow areas to have new peaks at 3056 cm$^{-1}$, 2207 cm$^{-1}$, 1663 cm$^{-1}$ and 1545 cm$^{-1}$ in addition to the disappearance of the N—H bands at 3357 cm$^{-1}$ and 3289 cm$^{-1}$. This corresponds to the spectrum expected for the poisoned catalyst. However, analysis of the other areas of the plates indicate that no poisoning has occurred. Indeed imine stretching was evident at 1612 cm$^{-1}$ from the condensation of benzaldehyde with the surface amine centres and it is this species that is believed to be the active catalyst for this reaction. The regions of poisoning on the flowcell plates can be attributed to non-uniform flow which results in localized areas of stationary flow and it is these areas which are susceptible to poisoning. If a catalytic coating was applied to microchannels with uniform flow, then continuous flow would inhibit the poisoning process and extend the life of these catalysts.

In another test with a higher loading of catalyst in the microchannel reactor, the plates were cleaned and modified with the silica coating. In this test, the silica coated plates were soaked in water for only 0.5 hour to remove sodium sulphate before treating with AMPS to tether the base catalyst. The plates showed much higher weight gains after catalyst preparation of 15.7 mg and 14.7 mg. Fresh reaction mixture was prepared and injected into the flowcell (preheated to 90° C.) via a syringe pump. After a residence time of 1 h (6.6 μLmin$^{-1}$) a conversion of 90% was found. For a flowrate of 24 μLmin$^{-1}$ (15 min residence time) a conversion of 70% was obtained. These results demonstrate the significantly higher yields at much shorter residence times when this type of catalyst is tethered to the walls of a microchannel reactor compared to conventional packed bed or packed microreactors.

Figure 5:
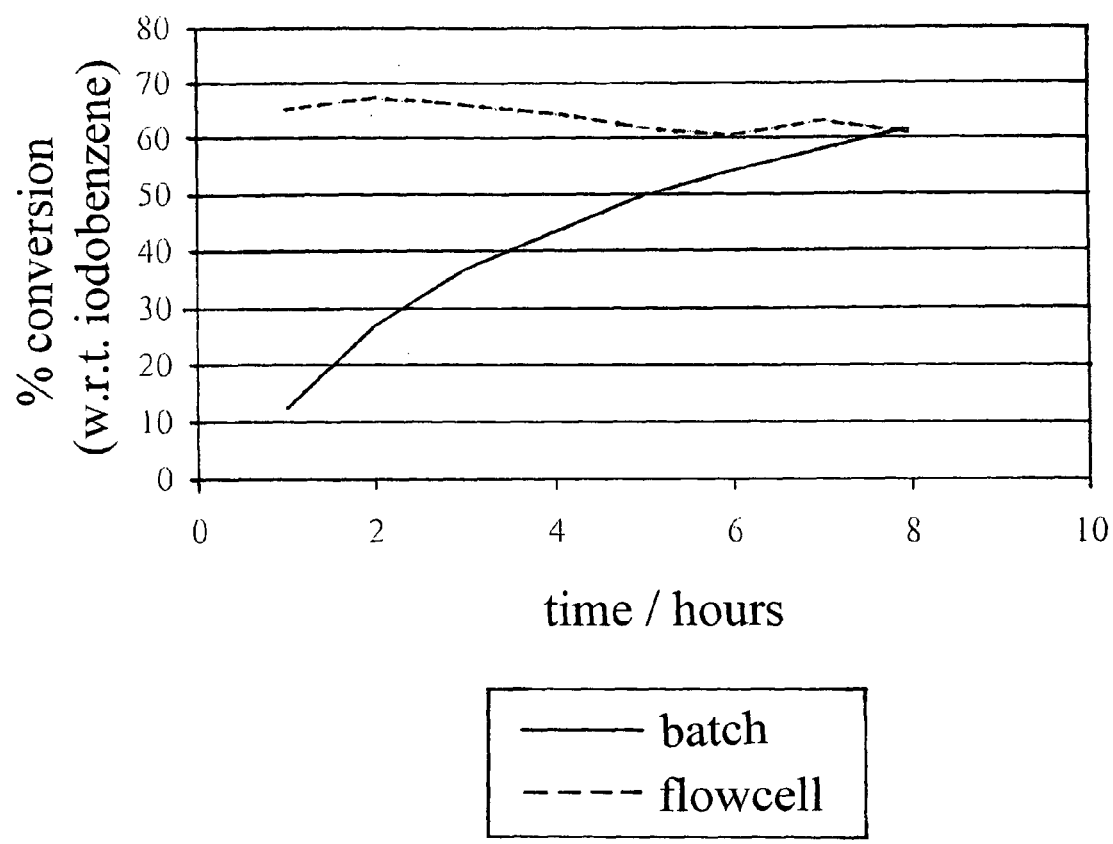
FIG. 5 is a plot showing conversion in the Knoevenagel reaction comparing conversion over a tethered catalyst in a microreactor system compared with a batch system over 8 hours.

A comparative test of the second pair of flowcell plates in batch conditions using AMPS derivatised silica (obtained from a modified aluminium surface 6×7 cm) was undertaken using the same amount of catalyst (5.4 mg). A reaction conducted over 8 h with 5.4 mg of catalyst and 3168 μL of reaction mixture (the volume passed through the cell during 8 h of flow) gave a conversion of 61.5% compared to an 8 h average of 63.5% through the flowcell (see FIG. 5).

The consistent levels of conversion of the flowcell would prove advantageous when applied to large scale synthesis allowing for long term feed without decline in activity, which in turn, would outperform large scale batch synthesis in terms of total turnover (especially given the tendency of these catalysts to undergo deactivation on isolation and re-use).

References 1. a) F. Knoevenagel, *Ber.*, 29, 172, 1896. b) F. Knoevenagel, *Ber.*, 31, 730, 1898
2. a) A. Corma, R. M. Martin-Aranda, V. Fornés and F. Rey, *J. Catal.*, 134, 58, 1992. b) A. Corma, V. Fornés, R. M. Martin-Aranda, H. Garcia and J. Primo, *Appl. Catal.*, 59, 237, 1990.
3. D. J. Macquarrie, J. H. Clark, A. Lambert, J. E. G. Mdoe and A. Priest, *React. & Funct. Polym.*, 35, 153, 1997.
4. S. M. Lai, R. Martin-Aranda and K. L. Yeung, *Chem. Commun.*, 218, 2003

Example 2

The Heck Reaction

The arylation and alkenylation of alkenes under the influence of a palladium catalyst has been extensively studied and applied to organic synthesis since the late 1960s[5]. The creation of new C—C bonds in the Heck Reaction is commonly catalysed homogeneously by palladium species generated from either Pd(0) compounds (e.g. [Pd(PPh$_3$)$_4$], [Pd$_2$(dba)$_3$]) or from Pd(II) salts (e.g. the acetate or chloride).

The model reaction system exemplified here is the coupling of iodobenzene with butyl acrylate to give butyl cinnamate.

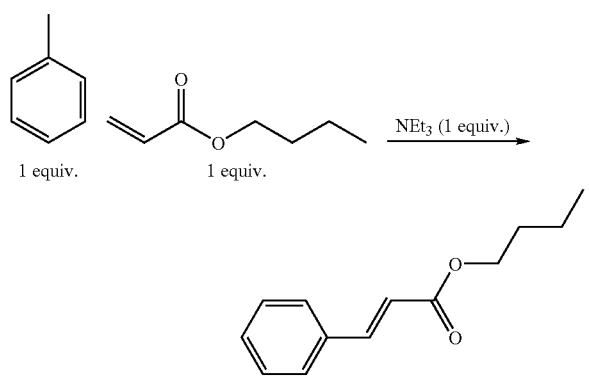

Preparation of Tethered Heck Catalysts.

The tethered catalysts used in these tests were based on a Schiff base palladium catalyst reported by Clark et al.[6] The active catalysts were tethered to silica coatings on the aluminium walls of the microchannel reactor. The preparation of the catalyst initially involves the modification of the silica coated aluminium surface with aminopropyl moieties that are subsequently converted to the Schiff base via condensation with 2-pyridine carbaldehyde. The Pd catalyst was then complexed to the Schiff base using palladium acetate in acetone as shown below.

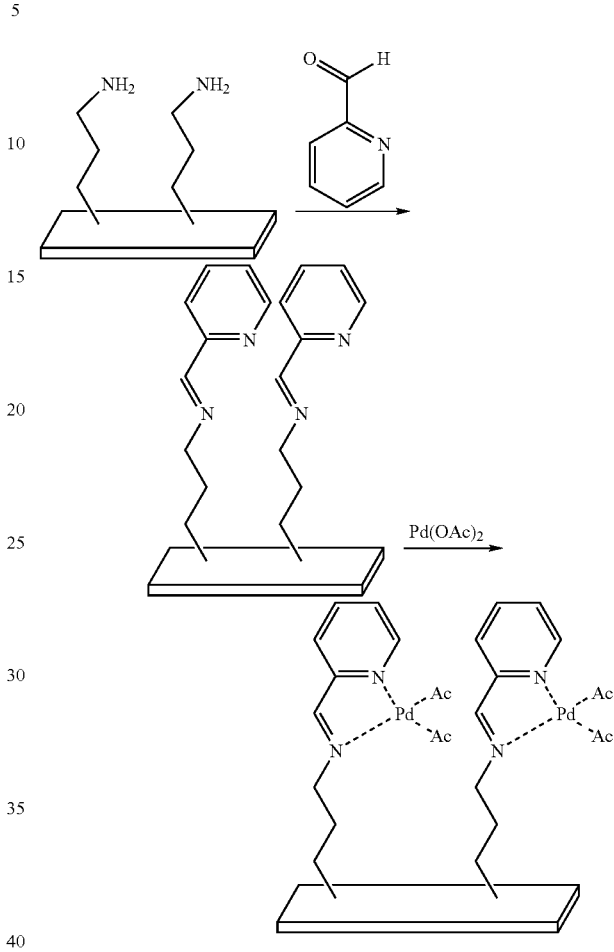

Aminopropyl modified silica coated plates prepared as for the Knoevenagel reaction above were placed in a 0.1 M solution of 2-pyridine carbaldehyde in acetonitrile (40 mL) and the mixture was set to reflux for 18 h. The plates were subsequently washed thoroughly with acetonitrile, dichloromethane and acetone before being dried in a vacuum oven (120° C.) for 1 h. The catalyst was formed via complexation with Pd(OAc)$_2$ in refluxing acetone (0.01 M, 20 mL) at room temperature over a 6 day period. The plates were then conditioned by placing in refluxing toluene (7 h) and then refluxing acetonitrile (7 h), before being dried in a vacuum oven (120° C.) for 1 h.

Heck Reaction Tests and Results

The microchannel reactor plates with the tethered Heck catalyst on their surfaces (weight gain of 10.4 mg and 11.7 mg) were assembled into the flowcell set up as above. The flowcell was heated using an electrical heating element clamped below the plates. This element was in turn connected to a variable resister that allowed for temperature control. The cell was lagged with cotton wool. A reaction mixture of iodobenzene, butyl acrylate and tri-n-butylamine (as base instead of triethylamine owing to its higher boiling point—216° C. as opposed to 89° C.) in 1,4-dioxane was injected into the flowcell, heated to 98° C., at a flow rate of 6.6 μLmin$^{-1}$. After 3 hours of continuous flow at a residence time of 1 hour no evidence of reaction was recorded. When the flow was stopped and a sample taken after 3 hours residence time a 17.1% conversion (w.r.t. iodobenzene) was noted. No evidence of erosion of the plates was observed.

Comparative tests on aluminium coupons with the Heck catalyst tethered to their surfaces showed no evidence of reaction in batch conditions after 1 h and much longer reaction times than those found above were required before significant conversion was obtained. Using triethylamine as base, batch activity tests were carried out for an aluminium slide segment (5 mm×5 mm). This was placed in an unstirred batch reactor (flask) with acetonitrile as solvent at reflux (82° C.). No reaction was observed after 1 hour. Conversions of 21% and 34% were only obtained after 10 hours and 24 hours respectively. This demonstrates that the tethered catalyst performs better in the microchannel reactor than in conventional batch conditions, achieving a similar conversion in one third of the time.

References

5. R. F. Heck, *J. Am. Chem. Soc.*, 90, 5518, 1968
6. E. B. Mubofu, J. H. Clark, D. J. Macquarrie, *Green Chem.*, 3, 23, 2001

Example 3

The Michael Reaction

The Michael reaction is a conjugate addition reaction that involves the formation of new carbon-carbon bonds. Typically this reaction is base catalysed employing bases such as diisopropylamine, potassium t-butoxide and tetramethylguanidine[7]. Heterogeneous catalysis of Michael reactions has been accomplished using systems such as KF and CsF on alumina[8], potassium t-butoxide on xonotlite[9] and Amberlyst A-27[10].

The model system exemplified here involves reaction between methyl vinyl ketone (but-3-en-one) and excess nitroethane.

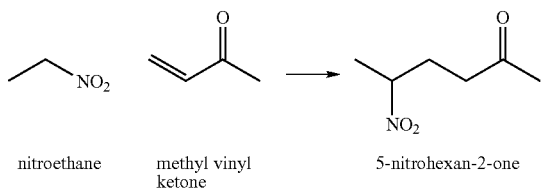

nitroethane     methyl vinyl ketone     5-nitrohexan-2-one

Preparation of the Tethered Catalyst for the Michael Reaction

The N,N-dimethylaminopropyl tethered catalyst shown below was prepared on the silica coated aluminium walls of the microchannel flowcell reactor.

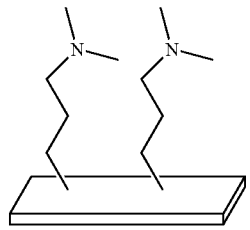

The modification of the reactor walls was a similar procedure to that used for the base catalyst (aminopropyl) used in the Knoevenagel reaction above, except that here N,N-dimethylpropylaminotrimethoxysilane was used to derivatise the silica coat. DRIFTS indicated successful modification with this dialkylaminosilane.

Michael Reaction Tests and Results

An aluminium coupon (25 mm×25 mm) was initially prepared to test the activity of the tethered catalyst for the Michael reaction in batch mode. The aluminium coupon's surface was coated with silica coat and organically modified with a solution of N,N-dimethylpropylaminotrimethoxysilane (10% v/v) in dichloromethane added dropwise. The plates were placed in an oven (100° C.) for 15 min. This process was repeated a further two times. The plates were then soaked in methanol for 1 h, rinsed with methanol and dried in a vacuum oven (120° C.) for 1 hour.

A segment of the slide (5 mm×5 mm) was placed in a small scale batch reactor which was set to reflux (102° C.). After 1 hour a conversion of 10% (w.r.t. methyl vinyl ketone) to a new peak (confirmed as 5-nitrohexan-2-one by GC-MS) was recorded by GC.

To compare performance in the microchannel flowcell, a pair of microchannel reactor flowcell plates modified with a silica washcoat and subsequently derivatized to form the base catalyst (weight gain of 20.1 mg and 15.4 mg) was assembled into the flowcell as above with a variable resister that allowed for temperature control. Fresh reaction mixture of nitroethane and methyl vinyl ketone was prepared and injected into the flowcell, heated to 98° C., at a flow rate of 6.6 µLmin$^{-1}$. Samples were collected and analyzed by GC and yields calculated from the calibration of an authentic sample of 5-nitrohexan-2-one with methyl vinyl ketone. After 7 hours of continuous operation, the flow was stopped and the cell cooled and disassembled in the atmosphere. The plates were washed thoroughly and no evidence of erosion was noted. The results are shown in the table below.

The flowcell was reassembled with the same plates after their exposure to air and the process repeated. On disassembly the plates were again washed and dried as before. They appeared to have developed a light yellow colour and weight loss of 1.8 mg and 0.8 mg was recorded. The process was then repeated a third time with the same plates. On this occasion a further weight loss of 4.2 mg and 3.5 mg was recorded.

| Sample time/ hours | Run 1 Yield (%) | Run 2 Yield (%) | Run 3 Yield (%) |
| --- | --- | --- | --- |
| 1 | 67 | 45 | 43 |
| 2 | 62 | 53 | 43 |
| 3 | 61 | 47 | 39 |
| 4 | 77 | 45 | 32 |
| 5 | — | 45 | 27 |
| 6 | — | 51 | 26 |
| 7 | 61 | 51 | 36 |

Yield for continuous flow experiment and subsequent re-uses with the same plates.

No evidence of side products (e.g. from Knoevenagel type condensations) was observed. During continuous flow steady yields were obtained with some fluctuation most likely the result of fluctuation in the microchannel reactor temperature. On repeat use, after exposure to air, some deterioration was apparent that was also reflected in the decrease in yields. This was most likely due to the exposure to air or moisture in the air between runs which could degrade the catalyst. This loss of activity would not be expected in the normal mode of operation in continuous commercial use. In conventional batch mode operation where separation and isolation of the catalyst would be required prior to re-use, some deactivation would be unavoidable.

The results in the microchannel continuous flow reactor are believed to be superior to the same tethered catalyst used in batch conditions, showing the benefits of using these catalysts in microchannel reactors including higher yields in shorter residence times and longer life.

References

7. J. E. Mdoe, J. H. Clark and D. J. Macquarrie, *Synlett.*, 625, 1998
8. J. H. Clark and D. G. Cork, *Chem. Lett.*, 1145, 1983
9. P. Laszlo and P. Pennetreau, *Tetrahedron Lett.*, 26, 2645, 1985
10. R. Ballini, P. Marziali and A. Mozzicafreddo, *J. Org. Chem.*, 61, 3209, 1996

What is claimed:

1. A catalytic system comprising a tethered catalyst composition disposed in a microchannel, wherein the microchannel comprises a bulk flow path, wherein the tethered catalyst composition comprises a solid support onto which has been immobilized an otherwise ordinarily molecular catalyst or procatalyst moiety; and
   wherein the microchannel comprises at least one wall and wherein at least one heat transfer microchannel is adjacent to the at least one wall of the microchannel.

2. The catalytic system of claim 1 wherein the tethered catalyst composition is attached to at least one wall of the microchannel that defines the bulk flow path in the microchannel.

3. The catalytic system of claim 1 wherein said tethered catalyst composition or tethered chiral auxiliary is provided as, or part of, a porous insert.

4. The catalytic system of claim 1, wherein said tethered catalyst composition comprises a solid support selected from the group consisting of: a solid inorganic oxide, carbon, an organic polymer, silica, alumina, a clay, a zeolite and a mesoporous solid.

5. A catalytic system comprising a tethered catalyst composition disposed in a microchannel, wherein the microchannel comprises a bulk flow path, wherein the tethered catalyst composition comprises a solid support onto which has been immobilized an otherwise ordinarily molecular catalyst or procatalyst moiety; and
   wherein the microchannel comprises at least one wall and the tethered catalyst composition is coated on the wall of the microchannel; and
tethered catalyst composition comprises a tether with at least a three atom chain.

6. The catalytic system of claim 5, wherein the tethered catalyst composition comprises one or more member selected from the group consisting of a metal, a metal coordination complex, an organometallic complex, an oxidant, a reductant, an acid, and a base.

7. A catalytic system comprising a tethered catalyst composition disposed in a microchannel, wherein the microchannel comprises a bulk flow path, wherein the tethered catalyst composition comprises a solid support onto which has been immobilized an otherwise ordinarily molecular catalyst or procatalyst moiety; and
   wherein the microchannel comprises at least one wall and the tethered catalyst composition is coated on the wall of the microchannel; and
further comprising a micromixer positioned to mix reactants prior to passage into the microchannel.

8. The catalytic system of claim 1 wherein the microchannel comprises at least one wall and a tethered catalyst or a tethered chiral auxiliary is coated on the wall of the microchannel.

9. A catalytic system comprising a tethered catalyst composition disposed in a microchannel, wherein the tethered catalyst composition comprises a solid support onto which has been immobilized an otherwise ordinarily molecular catalyst or procatalyst moiety; and
   wherein the microchannel comprises at least one wall and the tethered catalyst composition is coated on the wall of the microchannel; and
wherein the microchannel comprises a chiral auxiliary.

10. The catalytic system of claim 1, wherein the system comprises a tethered catalyst composition comprising a dendritic catalyst.

11. The catalytic system of claim 1 wherein the microchannel comprises a minimum dimension of greater than 1 µm and a length greater than 1 cm.

12. The catalytic system of claim 5, comprising at least one heat transfer microchannel that is adjacent to at least one wall of the microchannel.

13. The catalytic system of claim 12 wherein the at least one wall of the microchannel is comprised of an iron-containing alloy.

14. The catalytic system of claim 11 comprising at least 3 arrays of planar microchannels that comprise a tethered catalyst composition or a tethered chiral auxiliary disposed in the microchannels.

15. The catalytic system of claim 11 comprising at least 10 layers of heat exchangers interleaved with at least 10 layers comprising the microchannels that comprise a tethered catalyst composition or a tethered chiral auxiliary disposed in the microchannels.

16. The catalytic system of claim 11 comprising a bridging oxo group connecting a transition metal center of a tethered catalyst with a metal or semimetal on a surface of the interior of the microchannel.

17. The catalytic system of claim 1 wherein said tethered catalyst composition is made from an inorganic compound comprising $Ni[P(OMe)_3]_4$, $NiCl_2(PEt_3)_2$, $RhH(CO)(PPh_3)_3$, $RhCl(CO)(PPh_3)_2$, or $IrCl(CO)(PPh_3)_2$.

18. The catalytic system of claim 11 comprising at least 10 of the microchannels that comprise a tethered catalyst composition or a tethered chiral auxiliary disposed in the microchannel.

19. The catalytic system of claim 2 wherein the bulk flow path comprises a gap of 0.1 to 1.0 mm.

20. The catalytic system of claim 5 wherein the system comprises a tethered catalyst composition made by reacting $Cl-CH_2-CH_2-CH_2-SiH_3$, $Cl-CH_2-CH_2-CH_2-Si(OCH_3)_3$, or $Cl-CH_2-CH_2-CH_2-NH_2$ with a support surface.

21. The catalytic system of claim 1 wherein the system comprises a tethered catalyst composition made by reacting a metal complex with a tether that is subsequently reacted with an inorganic support.

22. The catalytic system of claim 1 wherein the system comprises a tethered catalyst composition comprising a tethered metallocene.

23. The catalytic system of claim 1 wherein the system comprises a tethered catalyst composition comprising a Schiff base palladium catalyst.

24. The catalytic system of claim 23 wherein a surface is modified with an aminopropyl tether.

25. The catalytic system of claim 9 wherein the microchannel comprises a bulk flow path.

26. The catalytic system of claim 1 wherein the microchannel comprises a cross section, and wherein the bulk flow path comprises at least 50% of the cross section of the microchannel.

27. The catalytic system of claim 1 wherein the microchannel comprises a cross section, and wherein the bulk flow path comprises 30% to 80% of the cross section of the microchannel.

28. The catalytic system of claim 1 wherein the tethered catalyst is in the form of a porous material in which at least 50% of the material's pore volume is in the size range of 0.1 to 300 μm.

29. The catalytic system of claim 1 wherein tethered catalyst composition comprises an amino-modified silica.

* * * * *